(12) United States Patent
Ouyang et al.

(10) Patent No.: US 11,395,579 B2
(45) Date of Patent: *Jul. 26, 2022

(54) PORTABLE ENDOSCOPE WITH DISPOSABLE STEERABLE CANNULA

(71) Applicant: UroViu Corp., Bellevue, WA (US)

(72) Inventors: Xiaolong Ouyang, Bellevue, WA (US); Chih-Yu Ting, New Taipei (TW); Shih-Ping Wang, Los Altos, CA (US)

(73) Assignee: UroViu Corporation, Bellevue, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/145,466

(22) Filed: Jan. 11, 2021

(65) Prior Publication Data

US 2021/0137352 A1 May 13, 2021

Related U.S. Application Data

(62) Division of application No. 16/447,251, filed on Jun. 20, 2019, now Pat. No. 11,013,396.

(51) Int. Cl.
*A61B 1/005* (2006.01)
*A61B 1/00* (2006.01)
(Continued)

(52) U.S. Cl.
CPC ........ *A61B 1/0052* (2013.01); *A61B 1/00048* (2013.01); *A61B 1/0057* (2013.01);
(Continued)

(58) Field of Classification Search
CPC ............ A61B 1/00048; A61B 1/00064; A61B 1/00066; A61B 1/00103; A61B 1/00105; A61B 1/00108; A61B 1/00121; A61B 1/00124; A61B 1/00126; A61B 1/00128; A61B 1/005; A61B 1/0051; A61B 1/0052; A61B 1/0053; A61B 1/0055; A61B 1/0056; A61B 1/0057; A61B 1/0058; A61B 1/008; A61B 2017/003; A61B 2017/00305; A61B 2017/00309; A61B 2017/00314; A61B 2017/00318; A61B 2017/00323;
(Continued)

(56) References Cited

U.S. PATENT DOCUMENTS 6,033,378 A * 3/2000 Lundquist ......... A61M 25/0147
604/95.01
6,221,007 B1 * 4/2001 Green ................ A61B 1/00052
600/106

(Continued)

*Primary Examiner* — Ryan N Henderson
(74) *Attorney, Agent, or Firm* — Wissing Miller LLP

(57) ABSTRACT

A handheld endoscope has a disposable, single-use portion that includes a fluid hub, cannula, distal tip and is steerable by the operator though actuation of one or two levers. The endoscope also includes re-usable portion that has a handle and display module. The distal tip includes LED illumination and an imaging module that feeds live video to the display module that is rotatable to allow viewing by the operator and others. The single-use and re-usable portions mate and un-mate with each other via physically separated mechanical and electrical connectors. The single use portion can include grasper device that can be actuated by an operator using an actuation tab.

18 Claims, 15 Drawing Sheets

(51) Int. Cl.
*A61B 1/307* (2006.01)
*A61B 17/00* (2006.01)

(52) U.S. Cl.
CPC ...... *A61B 1/00103* (2013.01); *A61B 1/00105* (2013.01); *A61B 1/00128* (2013.01); *A61B 1/00144* (2013.01); *A61B 1/00124* (2013.01); *A61B 1/307* (2013.01); *A61B 2017/00318* (2013.01); *A61B 2017/00323* (2013.01); *A61B 2017/00327* (2013.01)

(58) Field of Classification Search
CPC ........... A61B 2017/00327; A61B 2017/00331; A61M 25/0133; A61M 25/0136; A61M 25/0138; A61M 25/0141; A61M 25/0144; A61M 25/0147
See application file for complete search history.

(56) References Cited

U.S. PATENT DOCUMENTS

| | | | | |
|---|---|---|---|---|
| 6,793,882 B1* | 9/2004 | Verschuur | ................. | A61L 2/26 206/439 |
| 7,591,799 B2* | 9/2009 | Selkee | .............. | A61M 25/0147 604/95.04 |
| 7,606,609 B2* | 10/2009 | Muranushi | ............. | A61B 5/287 600/374 |
| 7,931,616 B2* | 4/2011 | Selkee | .............. | A61M 25/0136 604/95.04 |
| 8,197,398 B2* | 6/2012 | Scholly | .............. | A61B 1/00126 600/112 |
| 8,523,808 B2* | 9/2013 | Selkee | ............. | A61M 25/0136 604/95.04 |
| 8,998,844 B2* | 4/2015 | Reed | ................. | A61M 25/0097 604/95.04 |
| 9,736,342 B2* | 8/2017 | Mueckl | ................ | A61B 1/0052 |
| 2005/0277874 A1* | 12/2005 | Selkee | ............... | A61M 25/0136 604/95.04 |
| 2005/0277875 A1* | 12/2005 | Selkee | ................ | A61M 25/005 604/95.04 |
| 2007/0225556 A1* | 9/2007 | Ortiz | .................... | A61B 1/0684 600/172 |
| 2009/0225159 A1* | 9/2009 | Schneider | ......... | A61B 1/00022 348/82 |
| 2010/0069834 A1* | 3/2010 | Schultz | ............. | A61M 25/0147 604/95.04 |
| 2010/0168827 A1* | 7/2010 | Schultz | ............. | A61M 25/0136 607/116 |
| 2011/0054446 A1* | 3/2011 | Schultz | .................. | A61B 5/283 604/528 |
| 2011/0092775 A1* | 4/2011 | Deshmukh | ......... | A61B 17/0218 600/204 |
| 2012/0236138 A1* | 9/2012 | Liu | ...................... | G01N 21/954 348/84 |
| 2012/0286020 A1* | 11/2012 | Smith | ................. | A61B 17/072 606/1 |
| 2013/0324973 A1* | 12/2013 | Reed | ................. | A61M 25/0097 604/528 |
| 2014/0107416 A1* | 4/2014 | Birnkrant | ......... | A61B 1/00124 600/110 |
| 2014/0111634 A1* | 4/2014 | Mueckl | ................ | H04N 5/2252 348/82 |
| 2017/0188795 A1* | 7/2017 | Ouyang | ......... | A61B 1/00016 |
| 2018/0184892 A1* | 7/2018 | Truckai | ............. | A61B 1/00119 |
| 2018/0256009 A1* | 9/2018 | Ouyang | ......... | A61B 1/00052 |
| 2019/0246884 A1* | 8/2019 | Lu | ..................... | A61B 1/00142 |

* cited by examiner

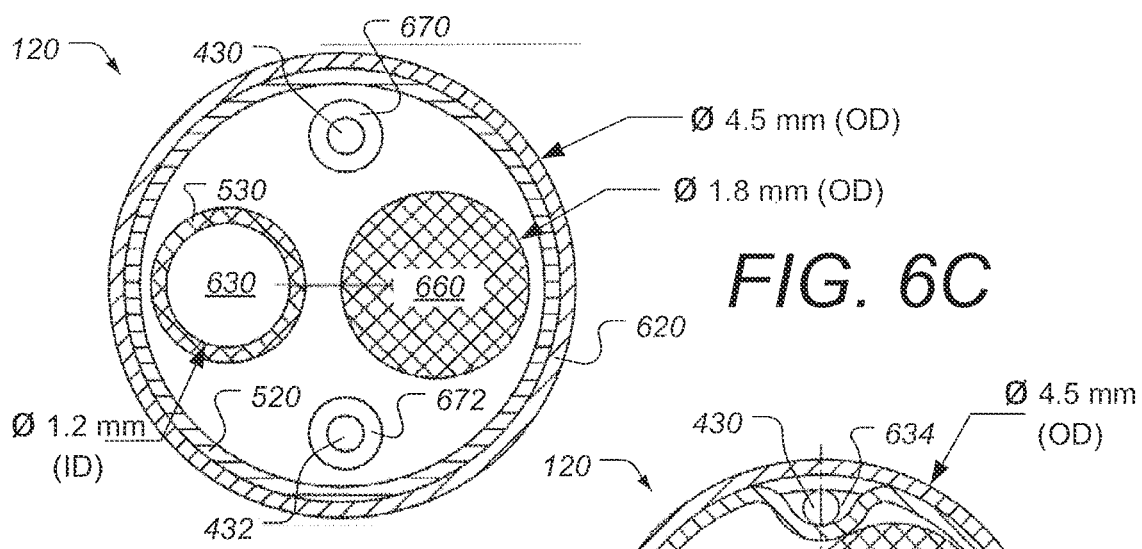
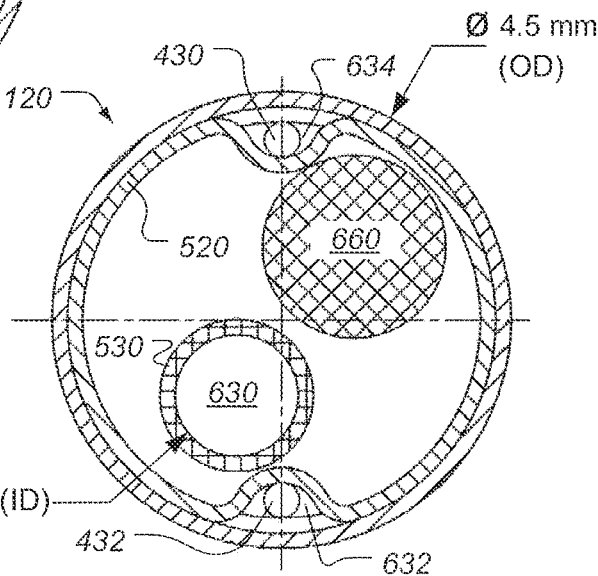
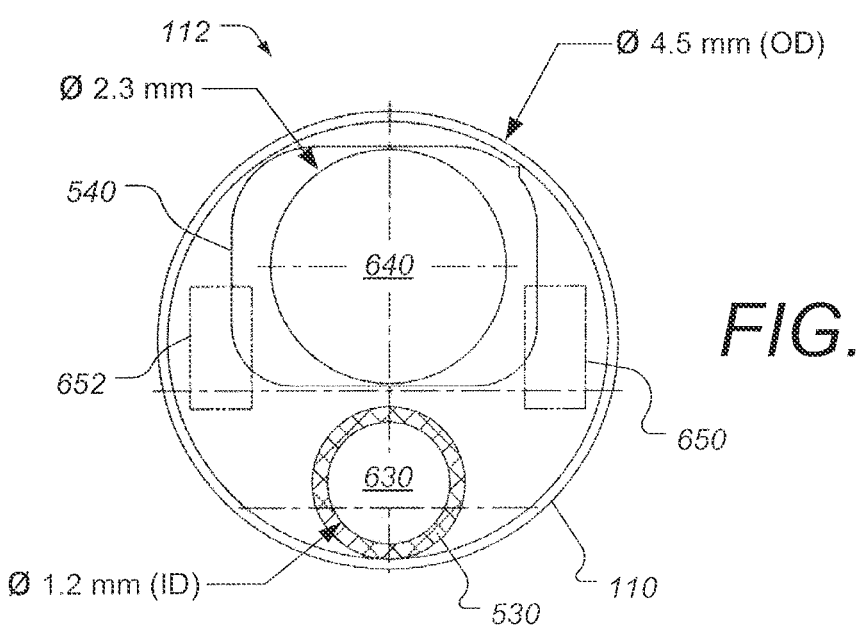

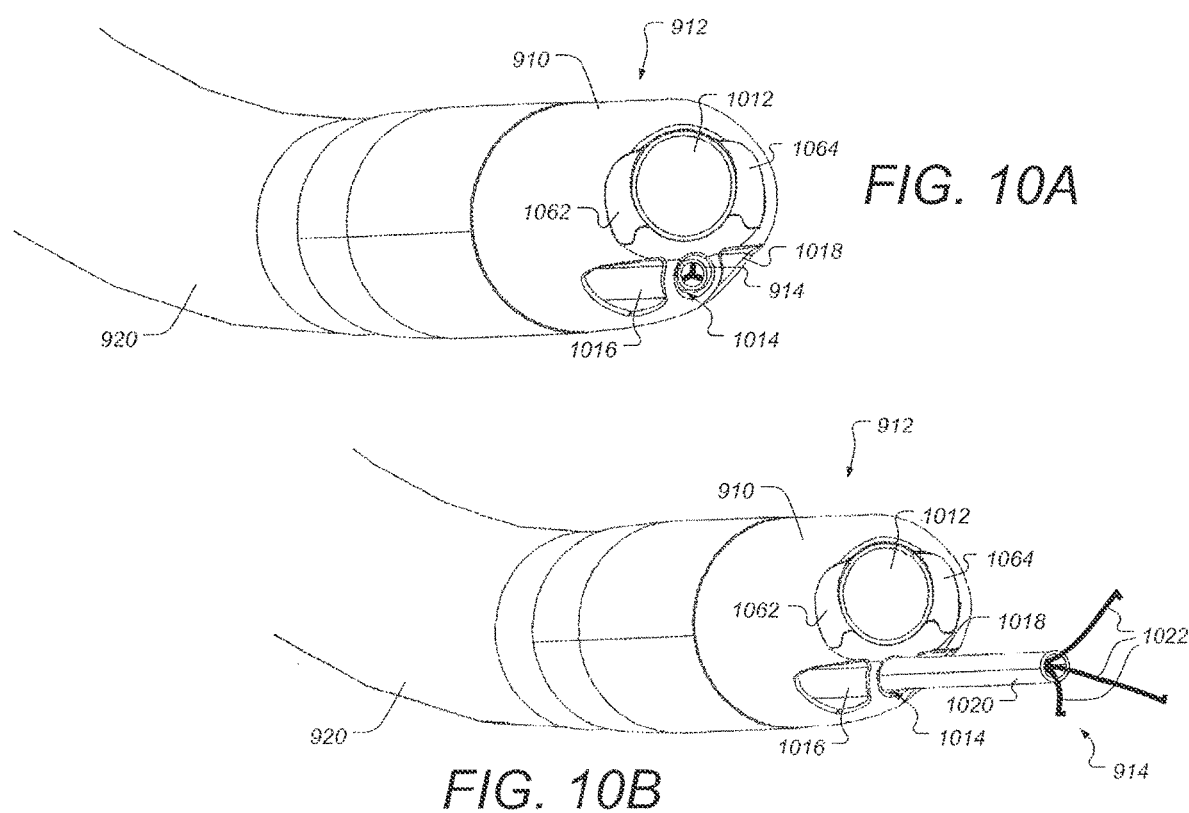

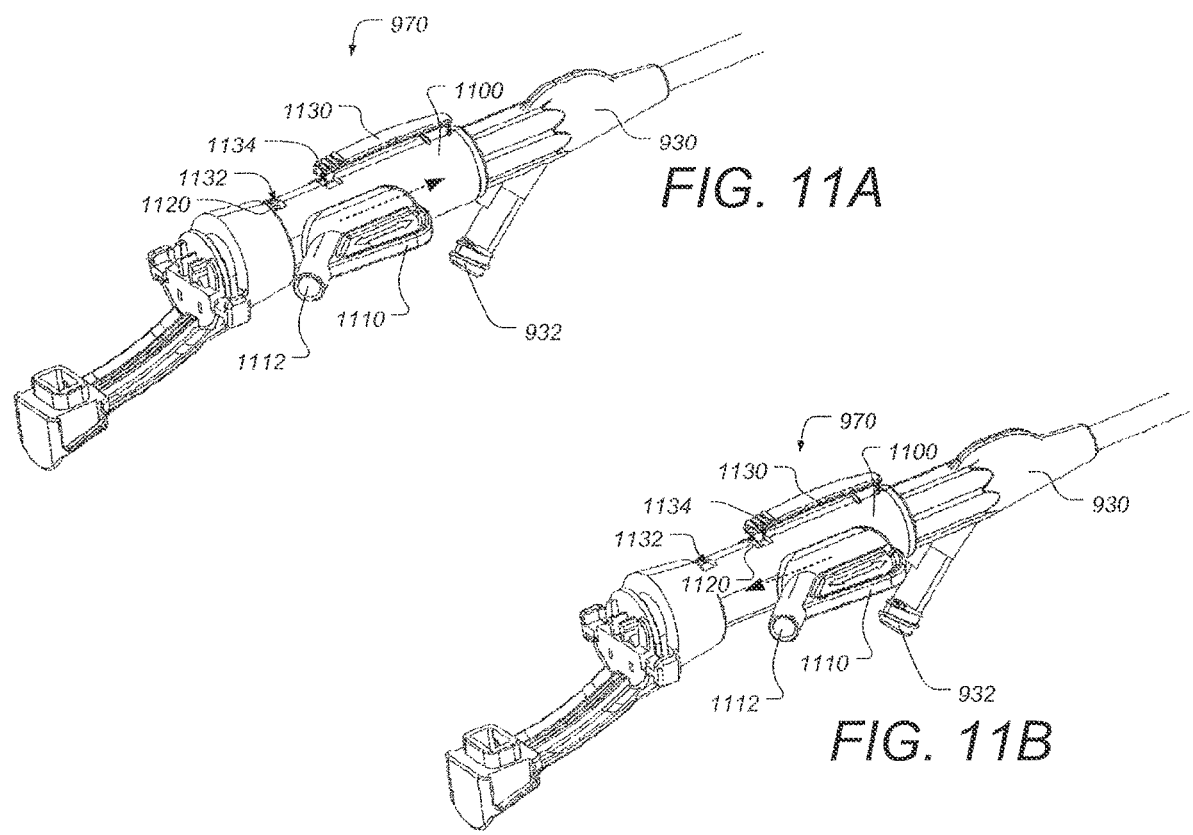

PORTABLE ENDOSCOPE WITH DISPOSABLE STEERABLE CANNULA

REFERENCE TO RELATED APPLICATIONS

This patent application claims the benefit of and incorporates by reference each of the following provisional applications:

This application is a divisional of application Ser. No. 16/447,251 filed Jun. 20, 2019 which claims priority to the following provisional patent applications:

U.S. Prov. Ser. No. 62/842,297 filed May 2, 2019;
U.S. Prov. Ser. No. 62/825,948 filed Mar. 29, 2019;
U.S. Prov. Ser. No. 62/821,536 filed Mar. 21, 2019;
U.S. Prov. Ser. No. 62/821,430 filed Mar. 20, 2019;
U.S. Prov. Ser. No. 62/797,235 filed Jan. 26, 2019;
U.S. Prov. Ser. No. 62/796,346 filed Jan. 24, 2019;
U.S. Prov. Ser. No. 62/795,042 filed Jan. 22, 2019;
U.S. Prov. Ser. No. 62/791,045 filed Jan. 11, 2019; and
U.S. Prov. Ser. No. 62/729,061 filed Sep. 10, 2018.

This patent application incorporates by reference each of the following provisional and non-provisional patent applications and issued patent(s):

U.S. Pat. No. 9,895,048 issued Feb. 20, 2018;
U.S. Pat. No. 10,278,563 issued May 7, 2019;
U.S. Pat. No. 10,292,571 issued May 21, 2019;
U.S. Ser. No. 15/856,077 filed Dec. 28, 2017;
U.S. Ser. No. 16/407,028 filed May 8, 2019;
U.S. Ser. No. 16/413,160 filed May 15, 2019;
U.S. Ser. No. 15/462,331 filed Mar. 17, 2017;
U.S. Ser. No. 15/371,858 filed Dec. 7, 2016;
U.S. Ser. No. 14/913,867 filed Feb. 23, 2016;
Intl Pat. App. No. PCT/US18/14880 filed Jan. 23, 2018;
Intl Pat. App. No. PCT/US16/65396 filed Dec. 7, 2016;
Intl Pat. App. No. PCT/US16/18670 filed Feb. 19, 2016;
U.S. Prov. Ser. No. 62/647,454 filed Mar. 23, 2018;
U.S. Prov. Ser. No. 62/634,854 filed Feb. 24, 2018;
U.S. Prov. Ser. No. 62/587,038 filed Nov. 16, 2017;
U.S. Prov. Ser. No. 62/551,264 filed Aug. 29, 2017;
U.S. Prov. Ser. No. 62/452,883 filed Jan. 31, 2017;
U.S. Prov. Ser. No. 62/449,257 filed Jan. 23, 2017;
U.S. Prov. Ser. No. 62/443,769 filed Jan. 8, 2017;
U.S. Prov. Ser. No. 62/416,403 filed Nov. 2, 2016;
U.S. Prov. Ser. No. 62/405,930 filed Oct. 9, 2016;
U.S. Prov. Ser. No. 62/375,814 filed Aug. 16, 2016;
U.S. Prov. Ser. No. 62/362,643 filed Jul. 15, 2016;
U.S. Prov. Ser. No. 62/339,810 filed May 21, 2016;
U.S. Prov. Ser. No. 62/299,453 filed Feb. 24, 2016
U.S. Prov. Ser. No. 62/287,901 filed Jan. 28, 2016;
U.S. Prov. Ser. No. 62/279,784 filed Jan. 17, 2016;
U.S. Prov. Ser. No. 62/275,241 filed Jan. 6, 2016;
U.S. Prov. Ser. No. 62/275,222 filed Jan. 5, 2016;
U.S. Prov. Ser. No. 62/259,991 filed Nov. 25, 2015;
U.S. Prov. Ser. No. 62/254,718 filed Nov. 13, 2015;
U.S. Prov. Ser. No. 62/139,754 filed Mar. 29, 2015;
U.S. Prov. Ser. No. 62/120,316 filed Feb. 24, 2015; and
U.S. Prov. Ser. No. 62/119,521 filed Feb. 23, 2015.

FIELD

This patent specification generally relates to a medical device for use in tissue examinations and endoscopic surgery such as in urology or similar fields. More particularly, some embodiments relate to a portable, handheld, low-cost surgical endoscope device having a steerable single-use portion and a multiple-use portion that is conveniently and effectively steerable.

BACKGROUND

Conventional endoscopy, or direct vision, used to examine the interior of a hollow organ or cavity of the body, uses a complex lens system for transmitting the image from the distal tip of the endoscope to a viewer. The lens system is typically a relay lens system in the case of rigid endoscopes or a bundle of fiber optics or an objective lens system in the case of flexible endoscopes. In the case of both rigid and flexible conventional endoscopes, the lens or fiber optic system is relatively expensive and is intended to be re-used many times. Therefore, stringent decontamination and disinfection procedures need to be carried out after each use.

In surgical procedures where a needle is used to inject fluid such as a drug into the patient's tissues, a long injection needle is inserted into the working channel of the endoscope. In such procedures, it is common to use two or more operators to carry out the surgical procedure: one to operate the endoscope and another to operate the needle assembly and syringe. It is common for there to be a physical separation between a display screen (e.g. mounted overhead), the endoscope (into the patient), and/or the syringe used to administer the drug. In such cases an operator or clinician has to look up to the display screen and cannot simultaneously view the scope handle and the syringe. Furthermore, the separate needle assembly, which is often long and somewhat cumbersome, needs to be threaded through the working channel of the endoscope and substantial manual dexterity may be required to control the jabbing and injection process. In some procedures, endoscopes with deflectable distal portions may be suggested, for example as discussed in U.S. Pat. Nos. 8,834,357 and 8,845,522.

Disposable endoscopy is an emerging category of endoscopic instruments. In some cases the manufacture of endoscopes can be made inexpensive enough to be used on a single patient only. Disposable or single-use endoscopy lessens the risk of cross-contamination and hospital acquired diseases. Partially disposable endoscopy systems are discussed in U.S. Pat. Nos. 9,895,048, 10,278,563, and 10,292,571 cited above. The subject matter described or claimed in this patent specification is not limited to embodiments that solve any specific disadvantages or that operate only in environments such as those described above. Rather, the above background is only provided to illustrate one exemplary technology area where some embodiments described herein may be practiced.

SUMMARY

Some embodiments that are particularly suitable for fields such as urology although the equipment and methods disclosed in this patent application can be used in other medical fields as well.

According to some embodiments, an endoscope comprises: a steering actuation hub and a cannula extending distally therefrom along a longitudinal axis and having a bendable distal portion; a pistol-grip handle to which the steering actuation hub and the cannula releasably attach to form said endoscope; and a finger-operated lever mounted to the endoscope for pivoting motion about a pivot axis transverse to said longitudinal axis. The lever is positioned to be engaged by a forefinger of a person holding said handle in a pistol-like grip. Cables operatively connect said lever with a distal portion of the cannula to cause said bendable portion of the cannula to bend relative to said longitudinal axis in response to pivoting said lever about said pivot axis.

The endoscope can further include an upwardly extending lever that also is positioned to be engaged by the forefinger of a person holding said handle in a pistol-like grip, and a connecting structure inside said steering actuation hub rigidly connecting to each other the upwardly and downwardly extending levers, in some embodiments. The connecting structure can comprise a wheel internally mounted in said steering actuation hub for rotation about said pivot axis, wherein said upwardly and downwardly extending levers are rigidly secured to said pivot wheel, according to some embodiments. The connecting structure can comprise pulleys rigidly secured thereto, and said cables can have proximal ends secured to an internal portion of the steering actuation hub away from said connecting structure and can run over said pulleys and then distally within the cannula, according to some embodiments. The lever can be configured to pivot in one direction to thereby bend the bendable portion of the cannula in one direction and pivot in an opposite direction to thereby bend the bendable portion of the cannula in an opposite direction. The bendable portion of the cannula can be configured to bend up from said longitudinal axis through an angle greater than down, for example to bend up from said longitudinal axis through an angle greater than 180 degrees and down through an angle less than 180 degrees. The cannula can be configured for insertion into a patient's bladder and said bendable portion of the cannula can be configured to bend up from said longitudinal axis through an angle greater than 180 degrees so that a field of view originating at a distal tip of the cannula includes the bladder neck. The lever can be a curved lever free of a lever guard, or the lever can be a loop positioned to accommodate a forefinger of a person holding the handle in a pistol-like grip and a lever connected at one end to said loop and at an opposite end to said connecting structure. The endoscope can further comprise an image display mounted on said handle, and can include mechanical and electrical connectors on each of said handle and hub, wherein the mechanical connector on the hub mates with that on the handle by relative motion in a direction transverse to said longitudinal axis, and said electrical connectors can be spaced proximally from said mechanical connectors by at least 5 cm when the endoscope is assembled by connecting the hub to the handle, in some embodiments. The hub and cannula can be prepackaged in a sterile package. The cannula can be mounted for rotation about said longitudinal axis relative to said handle.

In some embodiments, an endoscope comprises: a single-use disposable portion comprising a steering actuation hub and a cannula extending distally from said hub along a longitudinal axis and having a distal bendable portion; a pistol-grip handle to which the steering actuation hub and the cannula releasably attach to form said endoscope; and a lever extending from the hub and positioned to be engaged by the forefinger of a person holding said handle in a pistol-like grip. The lever can be mounted to the endoscope for pivoting motion about a pivot axis transverse to said longitudinal axis, and lines can operatively connect said lever with a distal portion of the cannula to cause said bendable portion to bend relative to said longitudinal axis in response to pivoting said lever about said pivot axis.

According to some embodiments, a method of viewing an interior of a patient's organ comprises: grasping an endoscope handle in a pistol-like grip; inserting into the patient's organ a cannula that extends distally from a hub intermediate the handle and the cannula; and bending a portion of the cannula that is in the patient's organ relative to a longitudinal axis of the cannula by pivoting a lever, with a forefinger of a hand grasping the handle, about a pivot axis that traverses said hub and is transverse to said longitudinal axis. The method can comprise pivoting about said pivot axis a first lever that extends downwardly from the hub and a second lever extending upwardly from said longitudinal axis, wherein the first lever bend the bendable portion of the cannula in one direction and the second lever bends the bendable portion in an opposite direction.

As used herein, the grammatical conjunctions "and", "or" and "and/or" are all intended to indicate that one or more of the cases, object or subjects they connect may occur or be present. In this way, as used herein the term "or" in all cases indicates an "inclusive or" meaning rather than an "exclusive or" meaning.

As used herein the terms "surgical" or "surgery" refer to any physical intervention on a patient's tissues, and does not necessarily involve cutting a patient's tissues or closure of a previously sustained wound.

BRIEF DESCRIPTION OF THE DRAWINGS

To further clarify the above and other advantages and features of the subject matter of this patent specification, specific examples of embodiments thereof are illustrated in the appended drawings. It should be appreciated that these drawings depict only illustrative embodiments and are therefore not to be considered limiting of the scope of this patent specification or the appended claims. The subject matter hereof will be described and explained with additional specificity and detail through the use of the accompanying drawings in which:

FIGS. 6C-6H are cross sections illustrating further details of a distal portion of an endoscope according to some embodiments;

FIGS. 10A and 10B are perspective views of a distal tip 912 and show aspects of the grasper actuation, according to some embodiments; and FIGS. 11A and 11B are perspective views showing aspects of grasper actuation for a handheld surgical endoscope, according to some embodiments.

DETAILED DESCRIPTION

A detailed description of examples of preferred embodiments is provided below. While several embodiments are described, it should be understood that the new subject matter described in this patent specification is not limited to any one embodiment or combination of embodiments described herein, but instead encompasses numerous alternatives, modifications, and equivalents. In addition, while numerous specific details are set forth in the following description in order to provide a thorough understanding, some embodiments can be practiced without some or all of these details. Moreover, for the purpose of clarity, certain technical material that is known in the related art has not been described in detail in order to avoid unnecessarily obscuring the new subject matter described herein. It should be clear that individual features of one or several of the specific embodiments described herein can be used in combination with features of other described embodiments or with other features. Further, like reference numbers and designations in the various drawings indicate like elements.

Figure 1A:
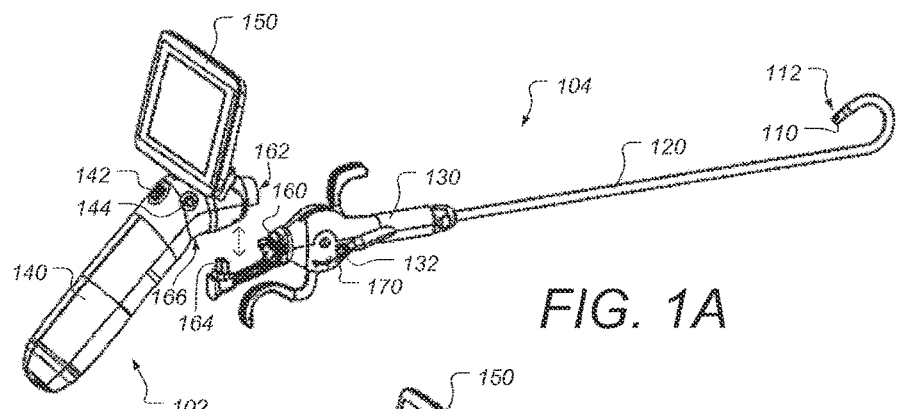
FIGS. 1A-1C are perspective views of a portable endoscope having a slim disposable steerable cannula, according to some embodiments.
Figure 1B:
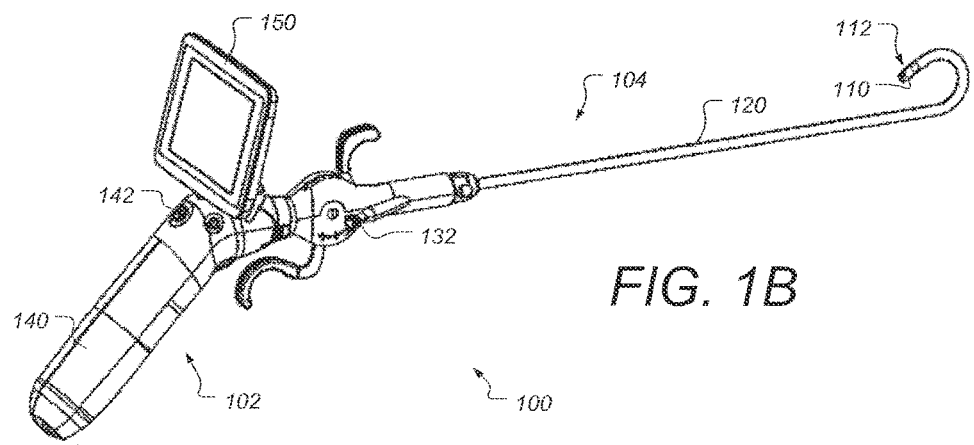
Figure 1C:
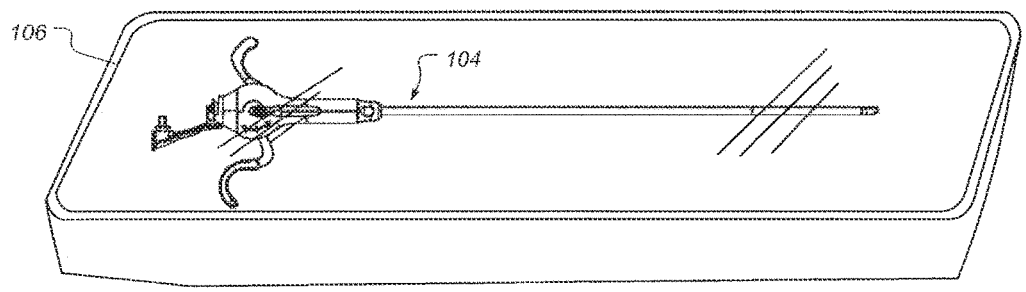

FIGS. 1A-1C are perspective views of a portable endoscope having a slim disposable steerable cannula, according to some embodiments. FIGS. 1A and 1B illustrate aspects of attachment and detachment of the single-use and reusable portions of handheld endoscope 100, according to some embodiments. The single-use portion 104 and reusable portion 102 attach mechanically primarily via mating mechanical connectors 160 and 162 as shown by the dotted arrow in FIG. 1A. Electrical connection is made via separate mating electrical connectors 164 and 166. In this example the two portions 102 and 104 are attached mechanically via translation vertically towards each other. Note that electrical connector 164 and mechanical connector 160 are both separated from the fluid hub 130, and are separated from each other by a distance of several cm, e.g., 5 cm or more. This separation allows for easy and effective, yet simple and inexpensive, fluid sealing to prevent fluid from hub 130, and any fluid from steering actuation hub 170 from penetrating internally towards connectors 160 and 164 and also allows some protection against any exterior fluid, for example from fluid port 132 from reaching and possibly compromising electrical connectors 164 and 166. The physical separation of the fluid hub 130 and the mechanical and electrical connectors 160 and 164 also provide additional assurance against accidental contamination from fluid hub 130 to the re-usable portion 102. For further details regarding the physical separation and associated benefits, see said U.S. Pat. No. 9,895,048.

The surgical endoscope 100 includes an elongated cannula 120 with a distal tip 112 for inserting into a hollow organ or cavity of the body. According to some embodiments, a separate distal tip sub-assembly 110 is attached to the cannula 120. According to some embodiments, the distal tip 112 is less than 4.5 mm in diameter when no working channel or a narrower working channel 630 is included in the cannula (FIGS. 6C-E). According to some embodiments, for example when a wider working channel 630 is included, the distal tip diameter can be 5.5 mm (FIGS. 6F-H). For further details relating to a separate tip sub-assembly for a handheld endoscope, see said: U.S. Pat. No. 9,895,048 (hereinafter referred to as "the '048 patent"); U.S. Ser. No. 15/462,331 filed Mar. 17, 2017 published as U.S. 2017-0188793 A1 (hereinafter the '331 application); and Int'l. Pat. App. No. PCT/US18/14880 filed Jan. 23, 2018 published as Int'l. Pub. No. WO/2018/136950 (hereinafter referred to as "the '880 application"). Sub-assembly 110 includes an imaging module and one or more LED light sources for viewing the organ or cavity into which tip assembly 110 is inserted. The tip assembly 110 also includes one or more fluid ports.

According to some embodiments, the cannula 120 includes one or more fluid channels which are fluidly connected to fluid port 132 at fluid hub and connection assembly 130. Port 132 includes a Luer fitting to facilitate leak-free connection of port 132 with various medical fluid components. The fluid channels or lumens in cannula 120 are also connected to a distal facing fluid ports of tip assembly 110. According to some embodiments, wires running from the LED light sources and camera module in tip assembly 110 pass through a separate channel in cannula 120.

The endoscope 100 includes a handle portion 140 that is sized and shaped in a pistol-like fashion for easy grasping by the endoscope operator (e.g. doctor or other medical professional). A display module 150 is rotatably mounted on handle 140 via a bearing which can be a plain bearing made of plastic, and a rubber coated hinge. Also visible on handle 140 are image capture button 142 and power button 144. According to some embodiments handle 140 and display module 150 are configured to be re-usable and make up reusable portion 102. According to some embodiments, handle 140 is like handle 140 shown and described in the '048 patent, the '331 application, and the '880 application.

Single-use portion 104 includes steering actuation hub 170, fluid hub and connection assembly 130, cannula 120 and tip assembly 110. Single-use portion 104 is made at a relatively low-cost and is intended to be disposed of after a single-use. By making the tip, cannula, fluid hub all single-use, stringent decontamination and disinfection procedures as well as the risk of cross-contamination and hospital acquired diseases can be significantly lessened or avoided. As shown in FIG. 10, according to some embodiments, the disposable, single-use portion 104 is sterilized, for example, during production and is provided to the user in a sealed sterilized pouch 106, for ease of storage and handling. According to some embodiments, a fluid line (not shown) is also included in single use portion 104 and can be attached to port 132 and included in the same sterilized pouch 106.

Figure 2:
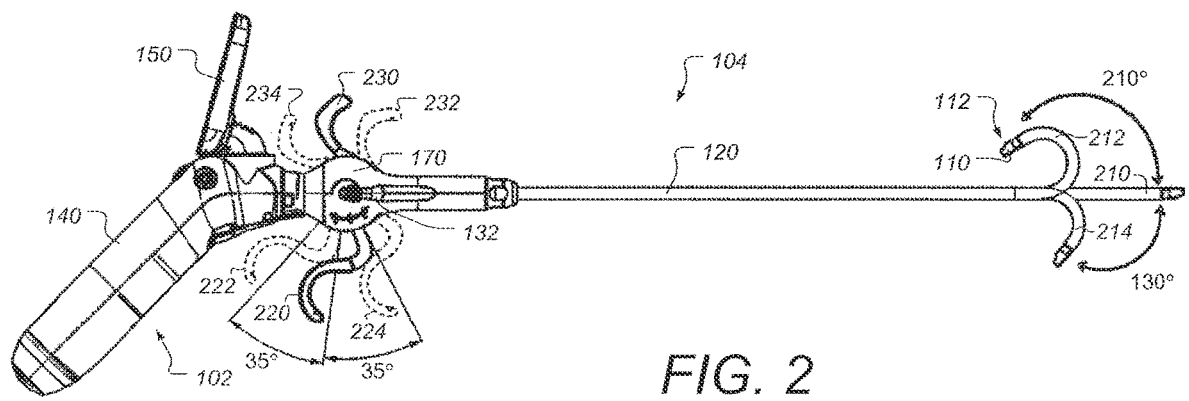
FIG. 2 is a side view of a slim disposable steerable cannula, according to some embodiments.

FIG. 2 is a side view of a slim disposable steerable cannula, according to some embodiments. The distal end of cannula 120 is controllably bendable in both the upwards and downwards directions as shown. The distal end of cannula 120 is shown in a neutral, or un-deflected position 210. The position 212 is an example of an extreme upwards deflection of 210 degrees, for example, while position 214 is an extreme downwards deflection of 130 degrees, for example. The deflection is controlled by one or two levers on the proximal end that extend from actuation hub 170. In this example there are two levers: lower lever 220 and upper lever 230. The lower and upper levers 220 and 230 are fixed together and rotate about the central axis of hub 170 such that when lower lever 220 is pulled proximally toward dotted position 222 the upper lever 230 will move distally toward dotted position 232. Likewise, when the upper lever 230 is pulled proximally toward dotted position 234 the lower lever 220 will move distally toward dotted position 224. In this example, when the lower lever 220 is pulled proximally, the distal end of cannula 120 and distal tip 112 is bent upwards toward position 212 and when the upper lever 230 is pulled proximally, the distal end of cannula 120 and distal tip 112 is bent downward toward position 213. In other examples the deflection relationships can be reversed. In this example pulling either lever 220 or 230 proximally by 35 degrees will result in actuation or deflection of the distal end of cannula 120 and distal tip 112 to bend to the extreme positions 212 (210 degrees up) and 214 (130 degrees down). In other embodiments, other amounts of deflection can be configured for various amounts of lever actuation.

Figure 3A:
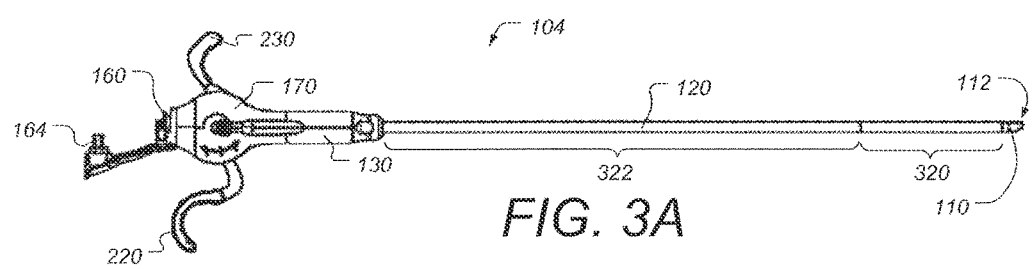
FIGS. 3A, 3B and 3C are right side, top and left side views, respectively, of a disposable steerable cannula, according to some embodiments.
Figure 3B:
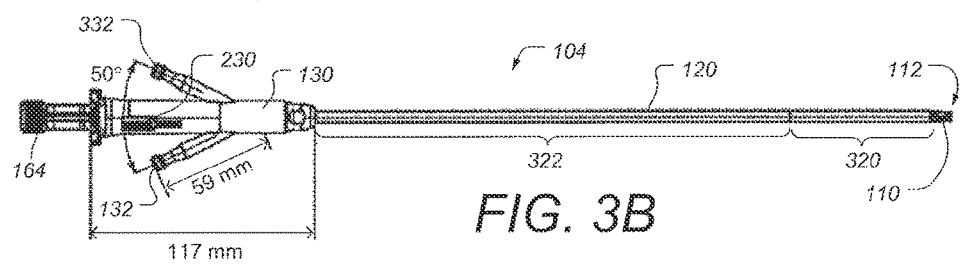
Figure 3C:
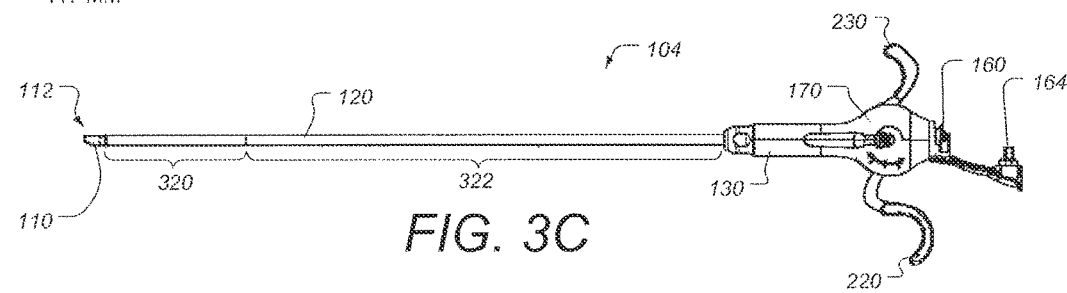

FIGS. 3A, 3B and 3C are right side, top and left side views, respectively, of a disposable steerable cannula, according to some embodiments. The cannula 120 is formed of a flexible portion 320 and a non-flexible portion 322. Also visible in FIGS. 3B and 3C is an optional second fluid and/or device port 332 on the left side of the fluid hub 130.

Figure 4A:
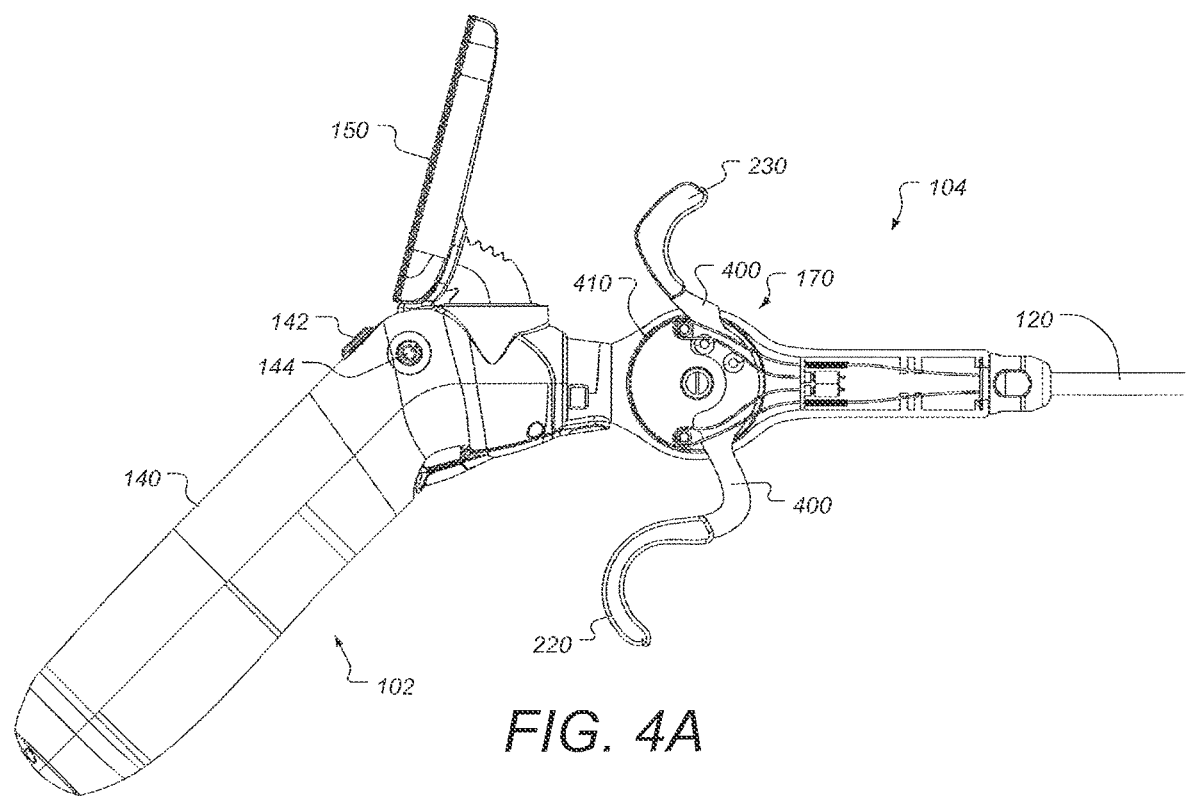
FIGS. 4A and 4B show further detail of an steering actuation hub of a portable endoscope having a slim disposable steerable cannula, according to some embodiments.
Figure 4B:
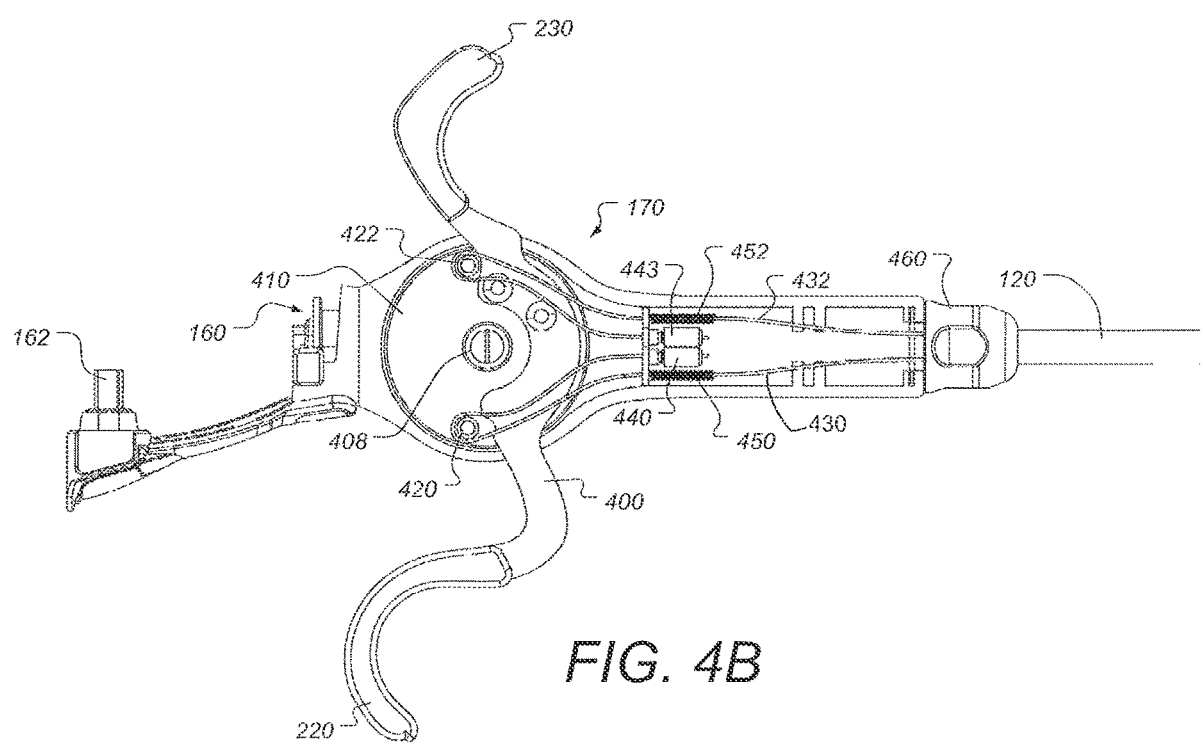

FIGS. 4A and 4B show further detail of a steering actuation hub of a portable endoscope having a slim disposable steerable cannula, according to some embodiments. The deflection is controlled by one or two levers that rotate a wheel 410 for pulling two cables 430 and 432 which actuate the deflection. FIG. 4A shows the proximal portion of disposable portion 104 mounted to the re-usable portion 102. FIG. 4B shows only parts of the disposable portion 104 for clarity. The lower and upper levers 220 and 230 are both fixed to, or form an integral part of, lever arm 400. Lever arm 400 is configured to rotate wheel 410 about its central axis 408. Attached to wheel 410 are two small pulleys: lower pulley 420 and upper pulley 422. Lower cable 430 is fixed by nut 440. The lower cable 430 runs through lower pulley 420 and guide 450 and then continues along the length of cannula 120 where it is fixed near its distal end (not shown). The upper cable 432 runs through upper pulley 422 and guide 452 and then continues along the length of cannula 120 where it is fixed near its distal end (not shown). As can be seen, when the lower level 220 is moved proximally, the wheel 410 will rotate clockwise. This will cause the lower pulley 420 to pull-on the lower cable 430 while causing the upper pulley to slacken the upper cable 432. The distal end of cannula 120 is configured to cause an upward deflection when cable 430 is tightened and cable 432 is slackened. Likewise, when upper lever 230 is moved proximally, the wheel 410 will rotate in a counter-clockwise direction. This will cause the upper pulley 422 to pull-on the upper cable 432 while causing the lower pulley to slacken the lower cable 430. The distal end of cannula 120 is configured to cause a downward deflection when cable 432 is tightened and cable 430 is slackened. For this purpose and in this non-limiting example, cables 430 and 432 cross before reaching the distal end of cannula 120 so that lower cable 430 is attached to an upper part of tip 112 and upper cable 432 is attached to a lower part of tip 112. Because of such crossing, pulling the lower lever 220 in the proximal direction bends the cannula's distal tip upwardly and pulling upper lever 230 bends the cannula's distal tip downwardly. Such cable crossing can take place distally of the actuation hub. Alternatively, the cables can cross within hub 170, for example by having cable 430 runs through guide 452 and attach to an upper portion of cannula tip 112 and having cable 432 run through guide 450 and attach to a lower part of cannula tip 112. It has been found desirable in some medical procedures to bent distal tip 112 upward by using the more natural motion of pulling lower gun lever 220 in the proximal direction, as in pulling a gun trigger. Upward bending, particularly through a larger angle, uniquely assists some medical procedures, such as procedures in which it is desirable to view the neck of a bladder by bending the cannula tip so much that the field of view of the endoscope is back, in the proximal direction.

Figure 5:
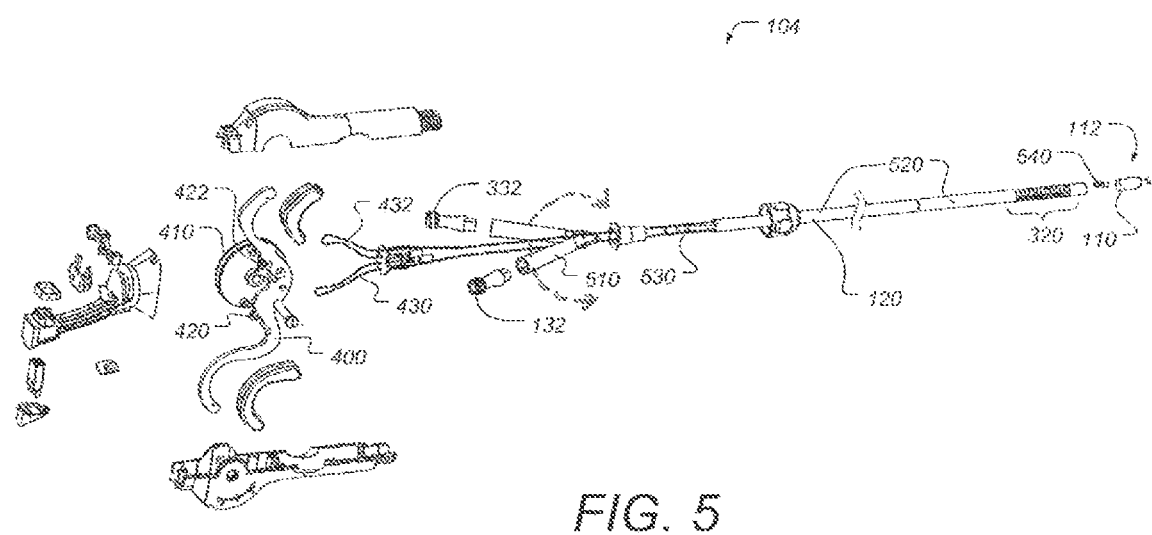
FIG. 5 is an exploded view illustrating various components of a disposable portion 104, according to some embodiments.

FIG. 5 is an exploded view illustrating various components of the disposable portion 104, according to some embodiments. Visible at the proximal end are the lever arm 400, wheel 410, pulleys 420 and 422, and upper and lower cables 432 and 430. Also visible are fluid/device conduits 510. Conduit 530 can be used as a device working channel and/or a fluid channel and is shown inserted in cannula 120. According to some embodiments, the cannula 120 is made of a steel tube 520 which has a series of notches cut in the flexible portion 320 that allow tube 520, and cannula 120 to bend upwards and downwards. At the distal end the flexible portion 320 of cannula 120 and tube 520 is shown distal tip piece into which fit camera module 540 and two LEDs.

Figure 6A:
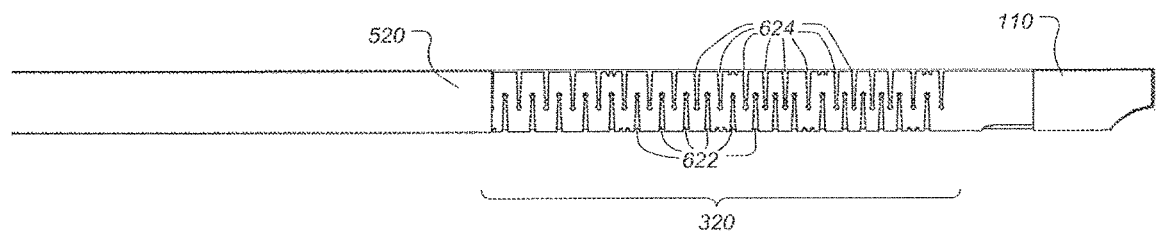
FIGS. 6A and 6B are a side view and perspective view and two cross sections, respectively illustrating further detail of a distal portion of an endoscope according to some embodiments.
Figure 6B:
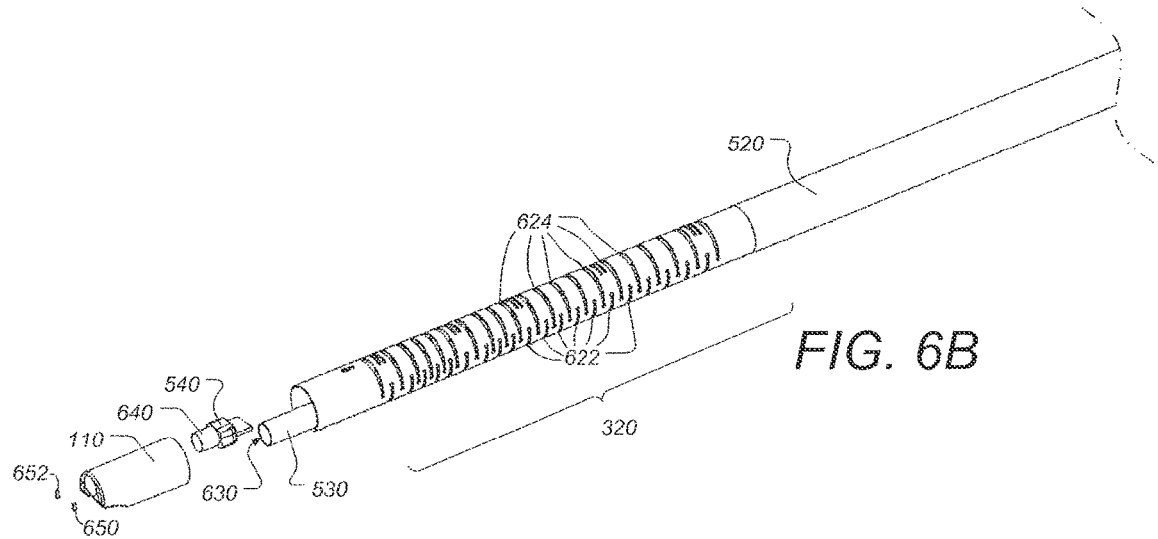
Figure 6F:
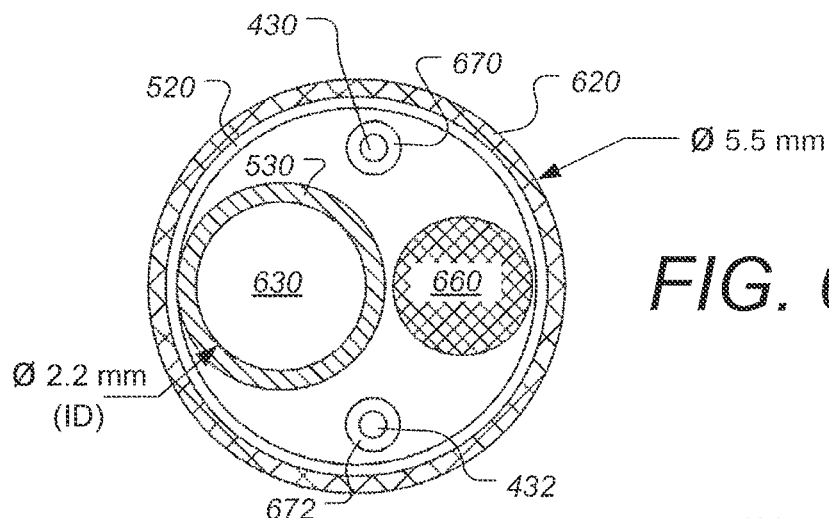
Figure 6G:
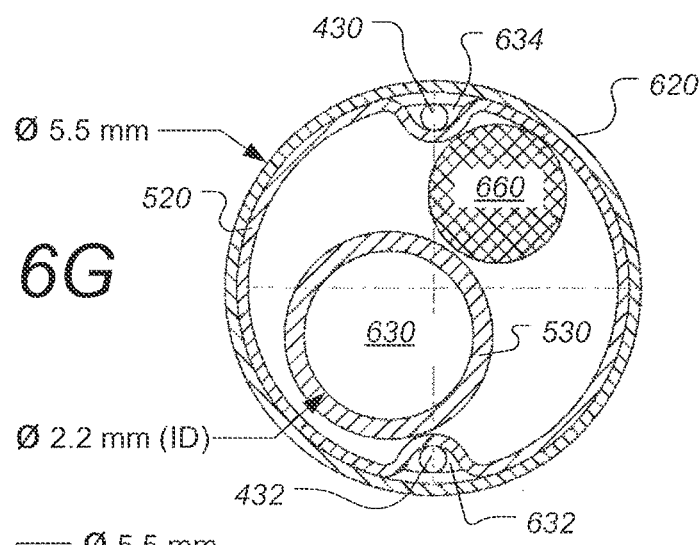
Figure 6H:
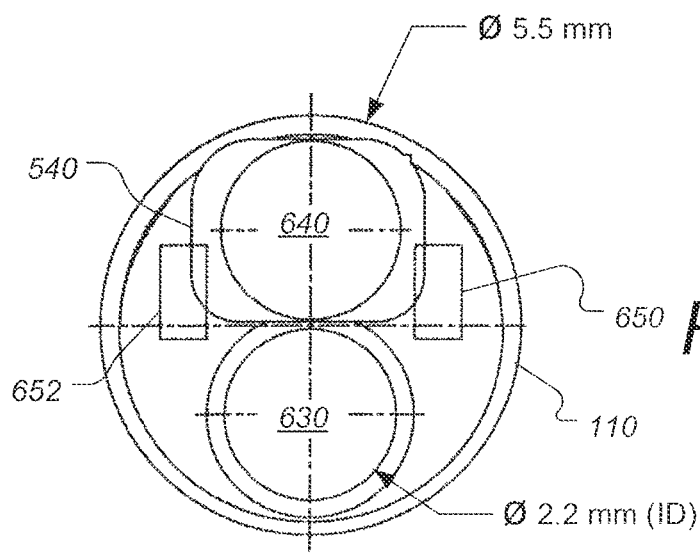

FIGS. 6A and 6B are a side view and a perspective view illustrating further detail of a distal portion of an endoscope according to some embodiments. Lower notches 622 and upper notches 624 that alternate and allow for upward and downward bending of tube 520 at flexible portion 320, are shown in greater detail. In FIG. 6B the conduit 530 is shown that can form working channel 630. The camera module 540 includes a lens portion 640 and fits into tip piece 110, as do LEDs 650 and 652.

FIGS. 6C-6H are cross sections illustrating further details of a distal portion of an endoscope according to some embodiments. FIGS. 6C, 6D and 6E are cross sections of the cannula 120 and distal tip 110 where the outer diameter of the cannula 120 and distal tip are 4.5 mm and the inner diameter of the working channel 630 is 1.2 mm. FIG. 6C is a cross section of cannula 120 in a location proximal to the flexible portion 320. The steel tube 520 is shown in this case surrounded by a thin sealing outer layer 620 that is not shown in FIGS. 5, 6A and 6B for reasons of clarity. Outer layer 620 can be made of a material such as PTFE and in some cases can be installed around the entire outer surface of the cannula 120 and portions of tip 112 via heat-shrinking. The cables 430 and 432 are also shown, threaded through wire conduits 670 and 672 respectively. The conduits 670 and 672 can be made of stainless steel and run the length of the cannula 120 that is proximal to the flexible portion 320. Note that when comparing FIG. 6C with FIG. 4B, cable 430 crosses from the bottom cable in FIG. 4B to the upper cable in FIG. 6C and cable 432 crosses from the upper cable in FIG. 4B to the lower cable in FIG. 6C. The location where the cables cross over, according to some embodiments, in proximal to the cannula 120 such as within housing 460 shown in FIG. 4B.

FIG. 6D is a cross section of cannula 120 in the flexible portion 320. In this location, the wires 430 and 432 pass through conduits 634 and 632 respectively. Note that the distal ends of cables 430 and 432 are bonded within conduits 630 and 632, respectfully, at a location along tube 520 that is distal of the flexible portion 320 (and notches 622 and 624). Also visible in FIGS. 6C and 6D is electrical cable 660 which in these examples has an outer diameter of 1.8 mm. Cable 660 is used to transmit power and control information to the camera module 540 and LEDs in the distal tip and also to transmit image and video data from the camera module back towards the handle portion 140 (e.g. shown in FIGS. 1A and 1B). FIG. 6E is a cross section of the distal tip 112 showing the lens portion 640 and camera module 540. The location of LEDs 650 and 652 are also shown in dash-dotted outline. According to some embodiments, the working channel 630 can be used for fluid infusion and also can contain a small guidewire. FIGS. 6F, 6G and 6H are cross sections of the cannula 120 and distal tip 110 in an example where the outer diameter of the cannula 120 and distal tip are 5.5 mm and the inner diameter of the working channel 630 is 2.2 mm. In this example the various components and materials are like the corresponding components and materials shown in FIGS. 6C-6E.

Further details relating to flexible portion 320 of cannula 120 and further aspects of steering and bending cannulae are provided in co-pending patent application U.S. Ser. No. 15/856,077 filed Dec. 28, 2017, published as U.S. Pat. App. Publ. US 2019/0059699 on Feb. 28, 2019, which is incorporated herein by reference.

Figure 7:
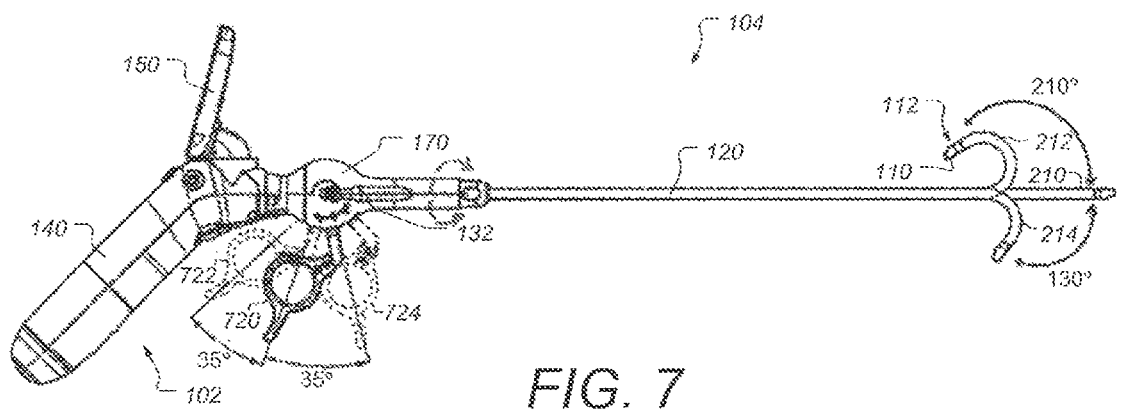
FIG. 7 is a side view of a slim disposable steerable cannula, according to some embodiments.

FIG. 7 is a side view of a slim disposable steerable cannula, according to some embodiments. The disposable portion 104 in this case is similar or identical in many respects as that described above except that the steering is controlled by a single lever 720 instead of two levers. The lever 720 is fixed to and rotates about the central axis of hub 170 such that when lever 720 is pulled proximally toward dotted position 722 the distal end of cannula 120 and distal tip 112 is bent upward towards position 212 and when the lever 720 is pushed distally toward dotted position 724, the distal end of cannula 120 and distal tip 112 is bent downward towards position 213. In other examples the deflection relationships can be reversed. In this example pulling or pushing lever 720 by 35 degrees will result in actuation or deflection of the distal end of cannula 120 and distal tip 112 to bend to the extreme positions 212 (210 degrees up) and 214 (130 degrees down). In other embodiments, other amounts of deflection can be configured for various amounts of lever actuation.

Figure 8:
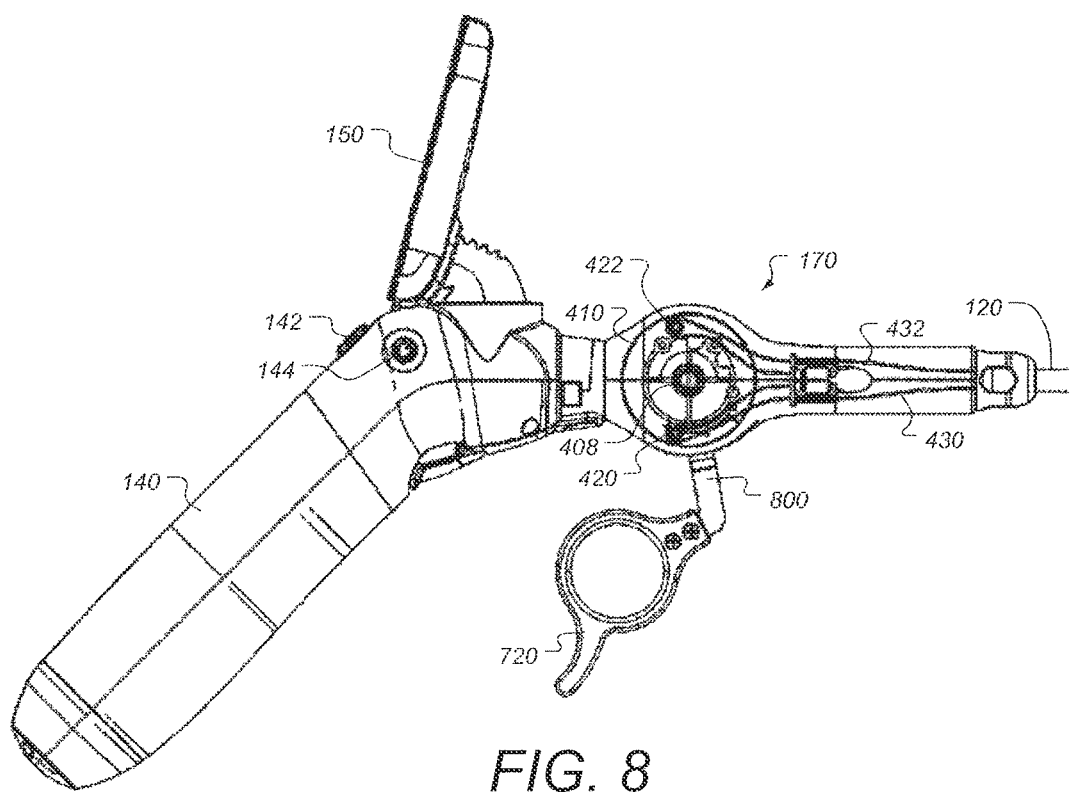
FIG. 8 shows further detail of a steering actuation hub of a portable endoscope having a slim disposable steerable cannula, according to some embodiments.

FIG. 8 shows further detail of an steering actuation hub of a portable endoscope having a slim disposable steerable cannula, according to some embodiments. The deflection is controlled by lever 720, which is fixed to arm 800 to rotate wheel 410. The rotation of wheel 410 pulls on or slackens cables 430 and 432 which actuate the deflection.

Figure 9A:
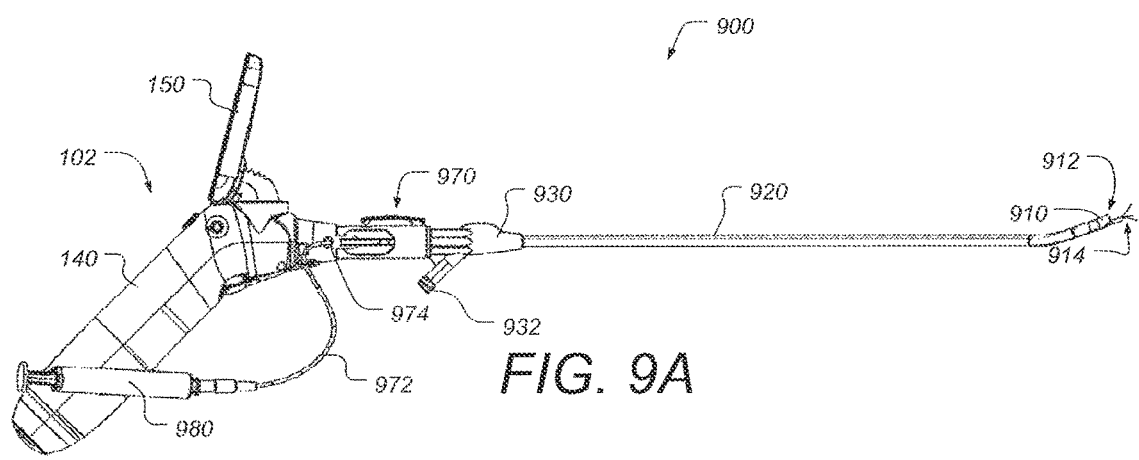
FIGS. 9A and 9B are a right side view a perspective view, respectively, of a handheld surgical endoscope having an integrated grasping tool, according to some embodiments.
Figure 9B:
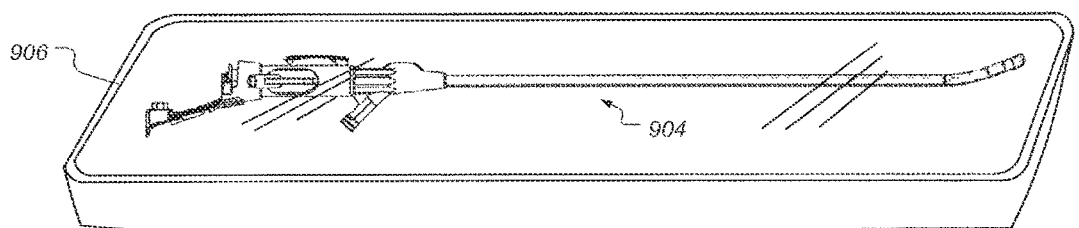

FIGS. 9A and 9B are a right side view a perspective view, respectively, of a handheld surgical endoscope having an integrated grasping tool, according to some embodiments. The surgical endoscope 900 includes an elongated cannula 920 with a distal tip 912 for inserting into a hollow organ or cavity of the body. A grasper 914 passes trough a dedicated lumen in cannula 920. The grasper 914 can be extended to protrude distally from distal tip 912 as shown. The grasper 914 can be attached to or formed as an integral part of a solid or hollow tube that can be actuated with actuation hub 970. In cases where grasper 914 includes a hollow tube, it can be in fluid communication with fluid line 972, which in turn is connected to syringe 980 (or other fluid dispensing device).

According to some embodiments, a separate tip sub-assembly 910 is attached to the cannula 920 which can be made from an extruded material. For further details relating to a separate tip sub-assembly for a handheld endoscope, see the '048 patent, the '331 application, and the '880 application. The tip assembly 910 includes an imaging module and one or more LED light sources for viewing the organ or cavity into which it is inserted. The tip assembly 910 also includes one or more fluid ports. The distal end of the cannula 920 can also be slightly bent as shown. According to some embodiments, a bend of about 15 degrees has been found to be suitable for many applications, but using other angles in alternative embodiments is not excluded.

According to some embodiments, the cannula 920 includes one or more fluid channels which are fluidly connected to fluid port 932 at fluid hub and connection assembly 930. Port 932 includes a Luer fitting to facilitate leak-free connection of port 932 with various medical fluid components. The fluid channels or lumens in cannula 920 are also connected to a distal facing fluid ports (orifice or ports 1016 and 1018 shown in FIGS. 10A, and 10B) of tip assembly 910. According to some embodiments, wires running from the LED light sources and camera module in tip assembly 910 pass through a separate channel in cannula 920.

Figure 12:
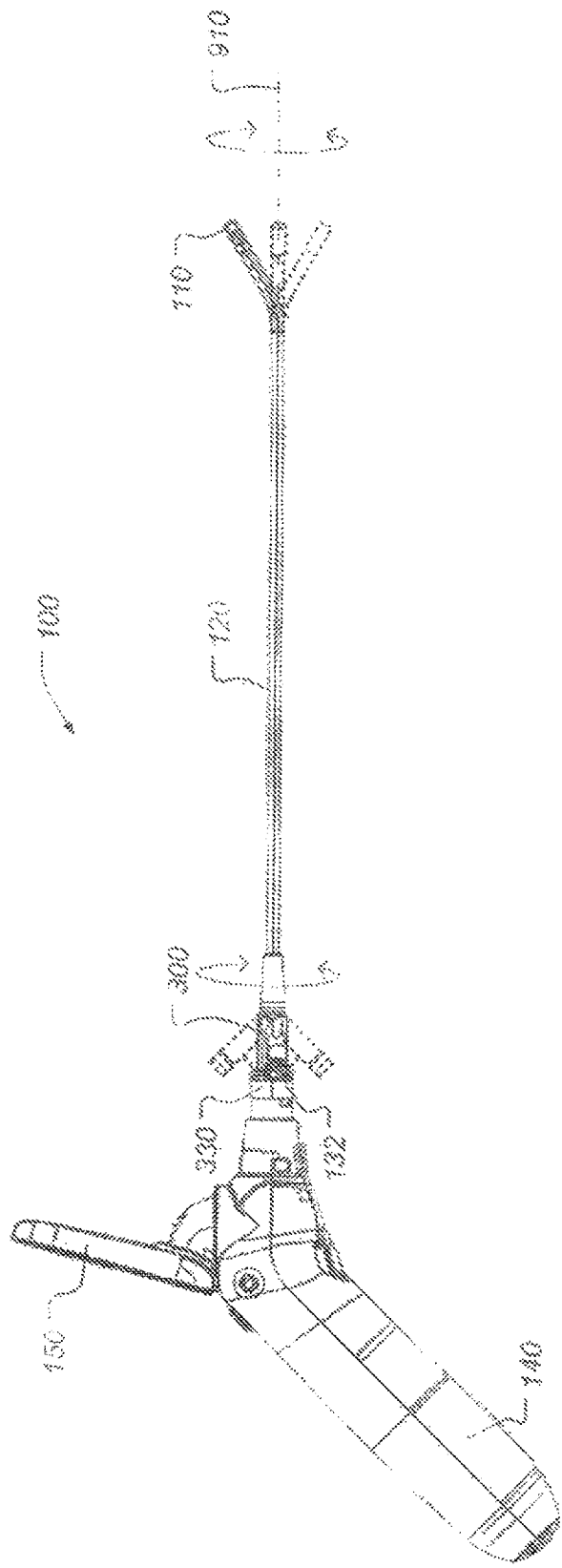
FIG. 12 is a side view of an endoscope with a rotatable cannula, according to some embodiments.

The endoscope 900 includes a handle portion 140 that is like handle portion 140 shown and described above and in the '048 patent and the '880 application. Single-use portion 904 includes needle actuation hub 970, fluid hub and connection assembly 930, cannula 920 and tip assembly 910. Single-use portion 104 is made at a relatively low-cost and is intended to be disposed of after a single-use. By making the tip, cannula, and fluid hub all single-use, stringent decontamination and disinfection procedures as well as the risk of cross-contamination and hospital acquired diseases can be significantly lessened or avoided. According to some embodiments the disposable, single-use portion 904 is sterilized, for example, during production and is provided to the user in a sealed sterilized pouch 906, for ease of storage and handling as shown in FIG. 9B. The camera module in the tip assembly can have a wide angle of view, such as 140 degrees in this example. According to some embodiments, the fluid line 972 is also included in single use portion 904 and can be attached to hub 970 and included in the same sterilized pouch 906. According to some embodiments, the surgical endoscope is configured to allow cannula 920 to rotate about its longitudinal axis. For further details of how to configure the hub 130 to allow rotation of the cannula, see the '048 patent, the '331 application, and the 880 application. FIG. 12 (which is the same as FIG. 9A of the '048 patent, illustrates rotation of the cannula 120 about a longitudinal axis, relative to handle 140. As disclosed in the '048 patent in connection with FIG. 9A therein, cannula 120 along with the distal tip 110 and fluid hub 300, is rotatable about main axis 910. The portion of the assembly that rotates with cannula 120 includes fluid port 132, fluid hub 300 and an inner tube that form the inner portion of sleeve bearing 330. Rotation of cannula 120 can be limited so that the internal electrical cable does not undergo undue stress from twisting. In one example starting from a "neutral" position shown in solid lines in FIG. 12, the cannula 120 can be rotated about 180 degrees in in either direction (i.e., clockwise or counter-clockwise). According to some other embodiments, an asymmetrical rotation pattern can be implemented in sleeve bearing 330 such as 270 degrees in one direction and 90 degrees in another direction. Many other combinations can be implemented, to improve ergonomics for various situations (i.e., various users, types of procedures, and patient anatomy variations). According to some embodiments, the rotation can be limited so as not to put undue stress on the internal electrical cable. FIGS. 5 and 7 include arrows indicative of rotation of cannula 120 relative to pistol-grip handle 140 about a longitudinal axis along which cannula 120 extends.

FIGS. 10A and 10B are perspective views of distal tip 912 and show aspects of the grasper actuation, according to some embodiments. FIG. 10A shows tip 912 when the grasper 914 in the retracted position while FIG. 10B shows tip 912 when the grasper 914 is in the extended position. Note that while in the retracted position, the claws of the 914 are fully recessed within grasper port 1014 of tip assembly 910 and there is no risk a sharps injury from the tip of grasper 914. Also visible in FIGS. 10A and 10B are camera lens dust cover 1012, two light-guide lenses 1062 and 1064 (for LED light sources) and distal fluid ports 1016 and 1018. The distal fluid ports 1016 and 1018 are provided to allow for fluid communication with the fluid lumina of cannula 920 (not shown). In this example, each of the fluid ports 1016 and 1018 have a cross sectional area of about 1.6 mm². Note that port 932, the cannula lumina and distal fluid ports 1016 and 1018 can be configured to provide fluid in-flow (i.e. flowing fluid out of the endoscope and into the patient's organ or cavity and/or fluid out-flow (i.e. flowing fluid out of the patient's organ or cavity and into the endoscope).

FIGS. 11A and 11B are perspective views showing aspects of grasper actuation for a handheld surgical endoscope, according to some embodiments. FIG. 11A shows the grasper actuation hub 970 when the grasper is in the retracted position as shown in FIG. 10A, while FIG. 11B shows the hub 970 when the grasper is in the extended position as shown in FIG. 10B. Hub 970 includes an outer housing 1100 through which are formed two windows, proximal window 1132 and distal window 1134. A lock release button 1130 extends from the housing 1100 and includes a inwardly protruding tab that aligns with distal window 1134. Actuation tab 1110 is moveable relative to the hub housing 1100. Moving with tab 1110 is fluid port 1112 that is in fluid communication with fluid line 972 (not shown), spring tab 1120 and grasper 914 (not shown). For further detail of the movable portions of hub 970, see FIG. 7B of the '331 application.

FIGS. 10A and 11A show the grasper 914 in the retracted position. In this positions, as mentioned the claws of grasper 914 are retracted within the grasper port 1014. In this retracted position, the distal tip 912 of the endoscope can be inserted into the organ and/or tissue of interest. When the operator observes on the display a target tissue that he/she wishes to manipulate, the actuation tab 1110 is pushed distally (as shown by the dotted arrow in FIG. 10A) until it is in the position shown in FIG. 10B. Using the display 150, the user then maneuvers the claws 1022 to be in a position surrounding the target tissue. In order to close the claws 1022, the actuation tab is moved proximally (as shown with the dotted arrow in FIG. 10B). It has been found effective in some cases to slide the endoscope distally at the same time as the actuation tab is moved proximally, so that the claws 1022 can remain in the same position relative to the target tissue. When the claws 1022 begin to engage with the distal rim of grasper port 1014, the claws 1022 begin to close upon each other. As the grasper is further retracted into the grasper port 1014, the grasping force of the claws 1022 increases. When the claws have sufficiently grasped the target tissue, the operator can then move the distal tip as appropriate to carry out the intended procedure.

The positions of the levers described above relative to the longitudinal axis of the cannula correspond to respective degrees of bending of the distal portion of the cannula, in some embodiments. A lever need not be subjected to additional force to keep it in position once the distal portion of the cannula has bent to a desired degree, except for any force that might be needed to overcome any tendency of the distal portion of the cannula to spring back toward an orientation along the longitudinal axis.

In some embodiments some, most, or all of the length of the cannula can be made of a material that is sufficiently flexible to allow the cannula to conform at least to some extent to curved body cavities or passages as it is inserted in the patient.

Although the foregoing has been described in some detail for purposes of clarity, it will be apparent that certain changes and modifications may be made without departing from the principles thereof. It should be noted that there are many alternative ways of implementing both the processes and apparatuses described herein. Accordingly, the present embodiments are to be considered as illustrative and not restrictive, and the body of work described herein is not to be limited to the details given herein, which may be modified within the scope and equivalents of the appended claims.

What it claimed is:

1. An endoscope comprising:
    a steering actuation hub and a cannula extending distally therefrom along a longitudinal axis and having a bendable distal portion;
    a pistol-grip handle to which the steering actuation hub and the cannula are releasably attached to form said endoscope;
    an elongated, rod-shaped first lever mounted to the steering hub for pivoting motion about a pivot axis transverse to said longitudinal axis and extending away from the steering hub in a first direction transverse to the longitudinal axis;
    an elongated, rod-shaped second lever mounted to the steering hub for pivoting motion about said pivot axis and extending away from the steering hub in a second direction that is transverse to the longitudinal axis and is different from the first direction;
    wherein each of said first and second levers is positioned relative to the handle to be engaged with a finger of a user holding said handle in a pistol-like grip; and
    cables operatively connecting said first and second levers with the bendable distal portion of the cannula to cause said bendable distal portion of the cannula to bend relative to said longitudinal axis of the cannula in response to pivoting said first and second levers about said pivot axis;
    wherein said bendable distal position of the cannula is configured to bend to an angle and in a direction relative to said longitudinal axis determined by degrees and directions of pivoting of said levers; and
    wherein said levers and cables are coupled to each other such that pulling the first lever through a first angle pivots the second lever distally and pushing said first lever distally bends said distal portion through a second angle different from the first angle and pivots the second lever proximally;
    wherein pulling the second lever proximally bends said distal portion of the cannula through said second angle and pivots the first lever distally and pushing said second lever distally and pushing said second lever distally bends said distal portion through said first angle and pivots the first lever proximally;
    wherein said bendable portion of the cannula is configured to bend through said first angle to a maximum angle that is less than a maximum angle through which said bendable portion is configured to bend in said second angle; and
    wherein said cannula is mounted for rotation about said longitudinal axis relative to said pistol-grip handle.

2. The endoscope of claim 1, further including a connecting structure inside said steering actuation hub rigidly connecting to each other said first and second levers, wherein holding both levers in a selected position maintains said bendable distal portion of the cannula at a selected angle.

3. The endoscope of claim 2, in which said connecting structure comprises a pivot wheel internally mounted in said steering actuation hub for rotation about a third pivot axis, wherein said first and second levers are rigidly secured to said pivot wheel.

4. The endoscope of claim 2, in which said connecting structure comprises pulleys rigidly secured thereto, and said cables have proximal ends secured to an internal portion of the steering actuation hub away from said connecting structure and run over said pulleys and then distally within the cannula.

5. The endoscope of claim 1, in which said first lever is configured to pivot to thereby bend the bendable portion of the cannula in a first angular direction and said second lever is configured to pivot to thereby bend the bendable portion of the cannula in a second angular direction opposite said first angular direction.

6. The endoscope of claim 1, in which said bendable portion of the cannula is configured to bend in said first angle through a maximum that is less than a maximum through which said bendable portion is configured to bend in said second angle.

7. The endoscope of claim 1, in which said bendable portion of the cannula is configured to bend in said first angle through a maximum less than 180 degrees and to bend in a second angle through a maximum that is more than 180 degrees.

8. The endoscope of claim 1, in which said cannula is configured for insertion into a patient's bladder and said bendable portion of the cannula is configured to bend in at least one of said first and second angles through more than 180 degrees so that a field of view originating at a distal tip of the cannula includes the bladder neck.

9. The endoscope of claim 1, in which at least one of said first lever and second lever comprises a curved lever free of a lever guard.

10. The endoscope of claim 1, further comprising an image display mounted on and mechanically supported by said handle.

11. The endoscope of claim 1, further comprising mechanical and electrical connectors on each of said handle and hub, wherein the mechanical connector on the hub mates with that on the handle by relative motion in a direction transverse to said longitudinal axis, and said electrical connectors are spaced proximally from said mechanical connectors by at least 5 cm when the endoscope is assembled by mating the hub to the handle.

12. The endoscope of claim 1, in which said hub and cannula are pre-packaged in a sterile package.

13. An endoscope comprising:
a single-use disposable portion comprising a steering actuation hub and a cannula extending distally from said hub along a longitudinal axis and having a distal bendable portion;
a pistol-grip handle to which the steering actuation hub and the cannula are releasably attached to form said endoscope;
wherein said cannula is mounted for rotation about said longitudinal axis relative to said handle;
an elongated first lever extending from the hub in a first direction transverse to said longitudinal axis and positioned to be engaged by a finger of a person holding said handle with the same hand in a pistol-like grip;
an elongated second lever extending from the hub in a second direction transverse to said longitudinal axis and positioned to be engaged by a finger of a person holding said handle with the same hand in a pistol-like grip;
each of said first and second levers being mounted to the steering actuation hub for pivoting motion about a pivot axis transverse to said longitudinal axis; and
lines operatively connecting said first and second levers with said distal bendable portion of the cannula to cause said distal bendable portion to bend relative to said longitudinal axis through a first angle in response to pivoting said first lever and through a second angle, opposite said first angle, in response to pivoting said second lever; and
wherein one of said first and second angles is more than 180 degrees and the other is less than 180 degrees.

14. The endoscope of claim 13, in which each of said first lever and second lever is positioned to be engaged by a finger of a person holding said handle with the same hand in a pistol-like grip, and further including a connecting structure inside said hub rigidly connecting said first and second levers to each other, wherein holding both levers in a selected position maintains said bendable distal portion of the cannula at a selected angle.

15. The endoscope of claim 14, in which said connecting structure comprises a pivot wheel internally mounted in said steering actuation hub for rotation about an axis transverse to said longitudinal axis, wherein said first and second levers are rigidly secured to said pivot wheel.

16. The endoscope of claim 13, in which each of said first and second levers is configured to pivot in one direction to thereby bend the distal bendable portion of the cannula in one angular direction from said longitudinal axis and to pivot in an opposite direction to thereby bend the distal bendable portion of the cannula in an opposite angular direction from said longitudinal axis.

17. The endoscope of claim 13, in which said distal bendable portion of the cannula is configured to bend in a first angular direction from said longitudinal axis through a maximum angle greater than 180 degrees and to bend in a second angular direction from said longitudinal axis through a maximum angle less than 180 degrees.

18. An endoscope comprising:
a steering actuation hub and a cannula extending distally therefrom along a longitudinal axis and having a bendable distal portion;
a pistol-grip handle to which the steering actuation hub and the cannula are releasably attached to form said endoscope;
wherein said cannula is mounted for rotation about said longitudinal axis relative to said pistol-grip handle;
an elongated, rod-shaped first lever mounted to the steering hub for pivoting motion about a pivot axis transverse to said longitudinal axis and extending away from the steering hub in a first direction transverse to the longitudinal axis;
an elongated, rod-shaped second lever mounted to the steering hub for pivoting motion about said pivot axis and extending away from the steering hub in a second direction that is transverse to the longitudinal axis and is different from the first direction;
wherein each of said first and second levers is positioned relative to the handle to be engaged with a finger of a user holding said handle in a pistol-like grip; and
cables operatively connecting said first and second levers with the bendable distal portion of the cannula to cause said bendable distal portion of the cannula to bend relative to said longitudinal axis of the cannula in response to pivoting said first and second levers about said pivot axis;

wherein said bendable distal position of the cannula is configured to bend to an angle and in a direction relative to said longitudinal axis determined by degrees and directions of pivoting of said levers; and wherein said levers and cables are coupled to each other such that pulling the first lever through a first angle and pivots the second lever distally and pushing said first lever distally bends said distal portion through a second angle different from the first angle and pivots the second lever proximally; and wherein pulling the second lever proximally bends said distal portion of the cannula through said second angle and pivots the first lever distally and pushing said second lever distally and pushing said second lever distally bends said distal portion through said first angle and pivots the first lever proximally.

* * * * *